United States Patent [19]

Butcher et al.

[11] Patent Number: 5,569,845
[45] Date of Patent: Oct. 29, 1996

[54] APPARATUS AND METHOD FOR DETECTING MOLTEN SALT IN MOLTEN METAL

[75] Inventors: Kenneth R. Butcher; Giulio A. Rossi, both of Hendersonville, N.C.

[73] Assignee: Selee Corporation, Hendersonville, N.C.

[21] Appl. No.: 442,478

[22] Filed: May 16, 1995

[51] Int. Cl.⁶ ........................................ G01N 27/04
[52] U.S. Cl. ................ 73/64.44; 73/61.41; 73/DIG. 9
[58] Field of Search ............... 73/64.44, 53.01, 73/61.41, 61.42, 61.43, DIG. 9; 75/384

[56] References Cited

U.S. PATENT DOCUMENTS 3,644,821  2/1972  Long ............................. 324/663
4,020,677  5/1977  Doddington et al. ............... 73/61.41
4,645,571  2/1987  Dubreuil et al. ................. 204/422 X
5,226,950  7/1993  Yu .

*Primary Examiner*—Hezron E. Williams
*Assistant Examiner*—Daniel Larkin
*Attorney, Agent, or Firm*—Carter & Schnedler

[57] ABSTRACT

There is provided an apparatus and method for detecting molten salt in molten metal. A pair of electrically conductive probes are immersed in the molten metal. The probes are connected to an electrical circuit which includes a voltage source and a current detector. The entire immersed portion of one of the probes is coated with an electrically nonconductive porous material which is wetted by molten salt but is not wetted by molten metal. If molten salt is present, the circuit will be completed and a substantial electrical current will flow between the probes, which current is detected by the current detector. If no salt is present, the circuit will not be completed and essentially zero current will be detected.

43 Claims, 2 Drawing Sheets

APPARATUS AND METHOD FOR DETECTING MOLTEN SALT IN MOLTEN METAL

BACKGROUND OF THE INVENTION

This invention relates to the production of metals. More particularly, it relates to the detection of the presence of molten salts in molten metals, such as Al or Al alloys.

In order to produce high quality metals, in particularly Al and Al alloys, filtration of the molten metals is employed to remove particulate contaminants or impurities. Those contaminants or impurities are typically removed by the use of ceramic filters. One such filter is described in U.S. Pat. No. 4,056,586 assigned to SELEE Corporation, assignee of this application.

In addition, other impurities, such as Na, Ca and $H_2$, are removed from the molten metal by adding reaction gases to react with those impurities which are more electrically positive than the Al. Often Ar, $Cl_2$, or $F_2$ gases and/or mixture thereof are injected into the molten Al alloys before filtration and casting in order to remove $H_2$ and to facilitate the floatation of solid impurities to the surface and their incorporation into the dross.

It is often difficult, however, for the operator of the metal production process to closely regulate the gas injection, and as a result, excess $Cl_2$ or $F_2$ can react with metals, such as Al and Mg to form salts. The existence of salts is particularly a problem where the salts are in a molten state at the temperatures of molten Al. NaCl and $CaCl_2$ are solids at molten Al temperatures, i.e. 750° C. and may be filtered from the molten Al by the ceramic filter. However, $MgCl_2$ and certain eutectic combinations of chlorides are in a liquid or molten state at molten Al temperatures and will not be filtered from the molten Al through conventional filters. These molten salts, which are suspended in the Al, become contaminant liquid or molten salts in the molten metal. The molten salts not only adversely affect the properties of the final Al alloy, but also reduce the efficiency of the filtration since the molten salt droplets adhere to solid impurities and prevent their collection by the filter and promote their release from the filter. This process of forming contaminant salts is sometimes referred to as chloridizing.

Applicant is presently unaware of the existence of a simple, inexpensive and reliable apparatus or method which can alert the operator when molten salt concentrations exceed maximum allowable limits established by metal producers.

One time consuming and labor intensive method of detecting these molten salts is done by withdrawing a sample of the molten metal, allowing it to cool and solidify, and cutting out a section. The section is analyzed by using a standard chemical or physical analytical technique. Obviously, such procedure is too time consuming. Typically, production cannot be stopped or delayed until an analysis is obtained.

U.S. Pat. No. 5,226,950 issued to Yu recognizes the problems associated with molten metal salts in molten Al. The Yu patent provides a method for detecting the presence of molten salts in the molten metal by a complex process. Yu calls for the introduction of a substantially inert gas into the molten metal, measuring the bubble size of the bubble formation of the gas in the metal, introducing a second liquid element into the metal to form a combination liquid, introducing a substantially inert gas into the combination liquid, measuring the bubble size formation of the gas in the combination liquid, and comparing the gas bubble size of the bubble formation of the first liquid with the gas bubble size of the bubble formation in the combination liquid. The Yu patent requires complex measuring apparatus to measure bubble frequency and bubble size.

OBJECTS OF THE INVENTION

It is therefore one object of this invention to provide a system for improving the quality of metal production, in particularly Al and Al alloys.

It is another object to provide a simple and inexpensive method and apparatus for detecting molten salts in molten metals.

It is yet another object to provide an inexpensive, simple and reliable technique for alerting the operator during molten metal production when molten $Cl_2$ or $F_2$ salt concentration exceeds the maximum allowable limit.

SUMMARY OF THE INVENTION

In accordance with one form of this invention there is provided a device for use in detecting the presence of molten salt in molten metal. The device includes a substrate adapted to be partially submerged in molten metal. The substrate, which preferably is in the form of a probe, includes an electrically conductive surface which is coated with an electrically nonconductive porous surface. Preferably, the nonconductive porous surface is a ceramic. The nonconductive surface is wettable by molten salt but is nonwettable by molten metal so that an electrically conductive path is established through the nonconductive surface by the presence of molten salts in the molten metal. Preferably, the ceramic nonconductive coating is a very thin coating made from a composition of CaO, MgO, $Al_2O_3$, $B_2O_3$ and $SiO_2$.

In accordance with another form of this invention, there is provided an apparatus for detecting the presence of molten salt in molten metal. A container is provided for receiving an amount of molten metal. A first substrate and a second substrate, which are not in direct physical contact with one another, are provided. Each of the substrates are partially submerged in the molten metal. The first substrate is constructed with a nonconductive coating as described above. The second substrate has a conductive surface but is preferably not coated with a nonconductive surface. An electrical circuit is connected to the first and second substrates. The electrical circuit includes a voltage source and a current detector. The current detector will detect a higher current in the circuit when the molten salt is present in the molten metal than when the molten salt is not present in the molten metal. Conversely, the electrical resistance of the circuit will be much higher when there is no molten salt present in the molten metal. Thus an Ohmmeter could be substituted for the current detector to measure the resistance as opposed to the current.

In accordance with yet another form of this invention, there is provided a method for producing a coated substrate for use in detecting the presence of molten salt in molten metal, including the following steps: forming a substrate having an electrically conductive surface; forming a slurry by combining a nonconductive material with water; adding a thickening agent and dispersant to the slurry, thereby forming a high viscosity slurry; coating the substrate with the high viscosity slurry; drying the coated substrate; and heating the dried coated substrate.

In still another form of this invention, there is provided a method for detecting the presence of molten salt in molten metal utilizing a container receiving an amount of molten metal including a first substrate and a second substrate, each of which are at least partially submerged in the molten metal, with the first substrate having an electrically conductive surface which is coated with an electrically nonconductive material, which is wettable by the molten salt but nonwettable by the molten metal, and the first and second substrates being connected to an electrical circuit, which method including steps of: applying a voltage to the circuit and measuring the current in the circuit, whereby the detection of no current or very little current indicates the lack of molten salt in the molten metal, and the detection of a high current indicates the presence of molten salt in the molten metal.

BRIEF DESCRIPTION OF THE DRAWINGS

The subject matter which is regarded as the invention as set forth in the appended claims, the invention itself, however together with further objects and advantages thereof, may be better understood with reference to the following description, taken in conjunction with the accompanying drawings, in which:

DESCRIPTION OF THE PREFERRED EMBODIMENT

Figure 1:
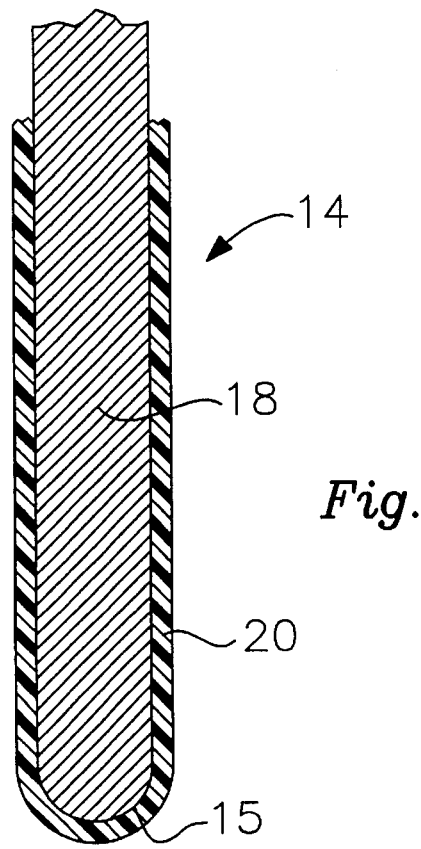
FIG. 1 is a partial sectional view of the probe of the subject invention.
Figure 2:
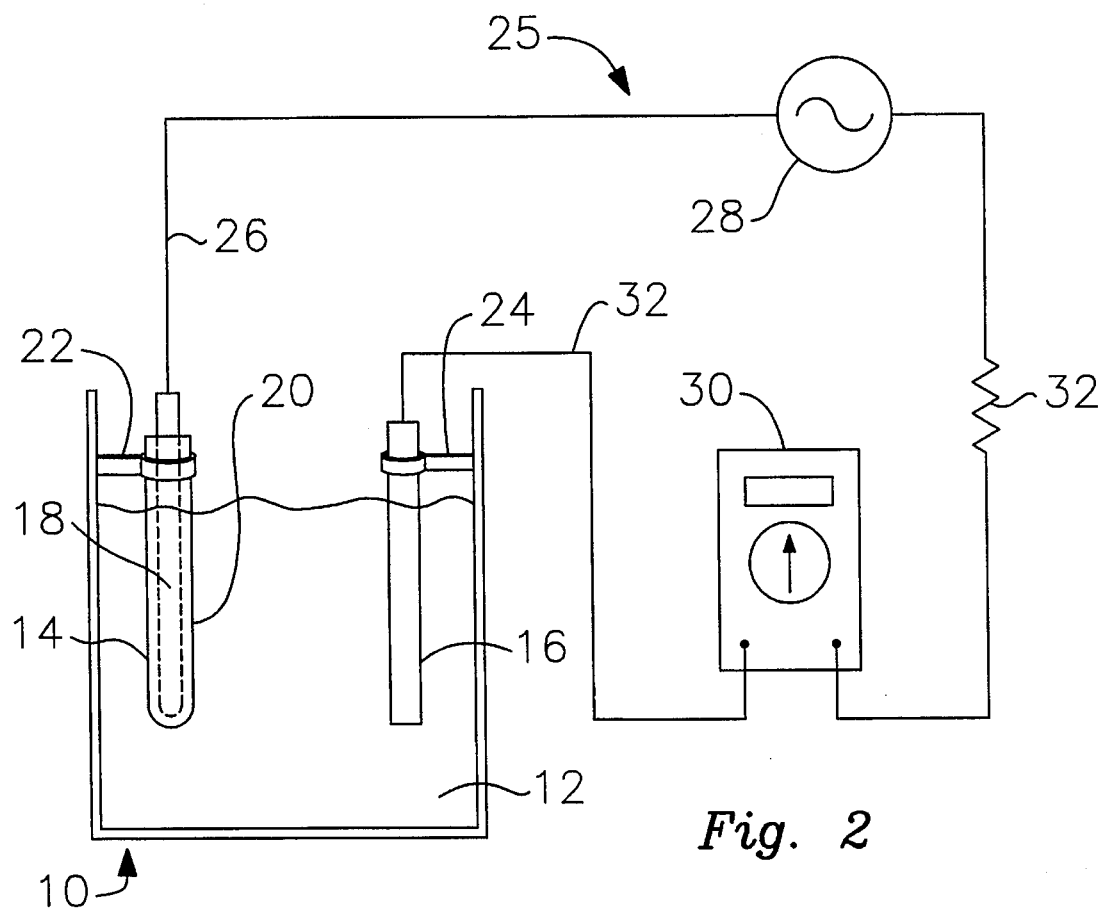
FIG. 2 is a schematic of the apparatus of the subject invention which utilizes the probe of FIG. 1.
Figure 3:
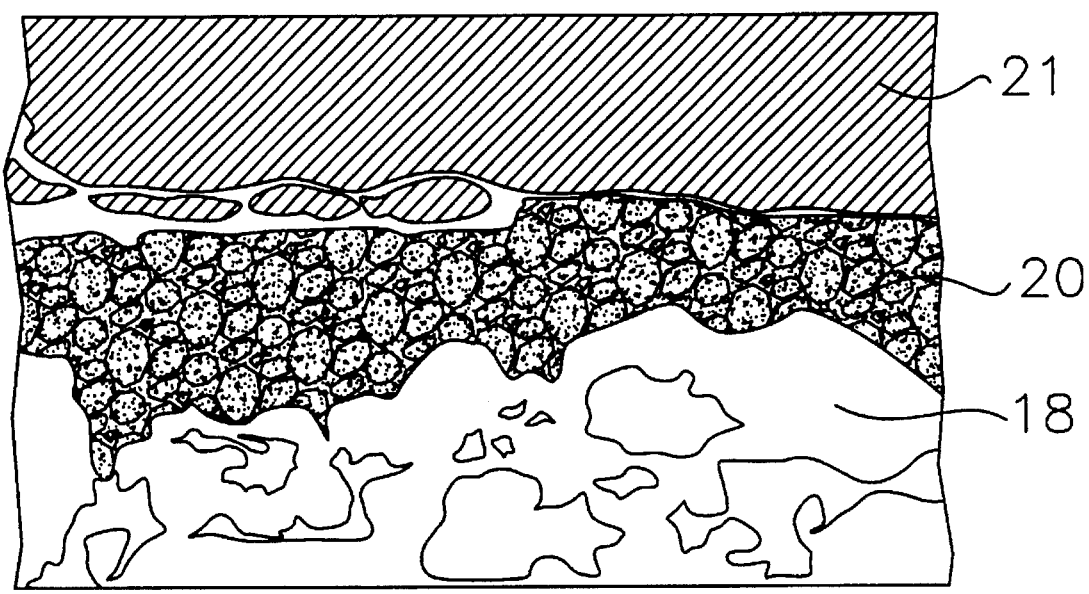
FIG. 3 is a photomicrograph showing details of the probe of FIG. 1.

Referring now more particularly to FIGS. 1 through 3, there is provided a container or vessel 10 which holds an amount of molten metal 12, which may or may not include an amount of molten salt therein. Preferably, the molten metal is Al or Al alloy. Substrate 14 is partially submerged in molten Al alloy 12. Substrate 16 is also partially submerged in the molten Al alloy 12. Substrates 14 and 16 are preferably in the form of elongated probes or rods. Probe 14 includes an inner rod 18 which is made of an electrically conductive material. Preferably, this electrically conductive material is a metal, conductive ceramic, or a metal/ceramic composite such as conductive Si/SiC or C/SiC. Preferably, the inner rod 18 is about 1 cm in diameter and 30 cm long. Acceptable rods are supplied by I$^2$R Corp., which are the same type of rods used as heating elements for electric furnaces. Preferably, the outer surface of the rod is rough to enhance the adhesion of the coating described below.

Probe 14 also includes an outer nonconductive coating 20. The coating must be nonconductive and porous to allow molten salts to penetrate into it, that is, the coating must be wettable by molten salts. The coating must be thin in order to detect small amounts of salts, but must completely cover that portion of the substrate which is immersed in the molten metal. Preferably, the thickness of the coating is between 0.001 millimeter and 8 millimeters. The coating should be nonreactive or inert towards Al and Al alloys. The adhesion of the coating 20 to the inner rod 18 must be strong to prevent spalling during operation. The coating must be nonwettable by the molten metal, i.e. the molten metal must not penetrate into the coating. The coating should contain essentially no cracks or pinholes which might allow contact of the molten metal with the rod 18. The coating should have a softening point significantly higher than the melt temperature of the metal to prevent sintering and the closure of its open pores. The probe should have good thermal shock resistance so that it will not crack when immersed into molten metal. The thermal expansion coefficients of the coating 20 and the inner rod 18 should be similar to prevent cracking of coating due to uneven thermal expansion. Finally, the probe should be easy to use, fairly inexpensive and reliable.

Preferably, coating 18 is a ceramic which is not wetted by molten metal. An acceptable ceramic coating 18 may be made from a frit supplied by Ferro Corp., designated frit #3249. This Ferro frit has a density of 2.4g/cm$^3$ and is a composition of 3.5% CaO, 12.2% MgO, 13.3% Al$_2$O$_3$, 28.9% B$_2$O$_3$ and 42.1% SiO$_2$. However, it is believed that the following ranges of that composition are acceptable: 0% to 5% CaO, 0% to 22% MgO, 2% to 50% Al$_2$O$_3$, 0% to 50% B$_2$O$_3$ and 15% to 80% SiO$_2$. It is believed that a ceramic composition omitting all of the components described above except for Al$_2$O$_3$ and Sio$_2$, will form a glass, which will provide acceptable results.

The thermal expansion coefficients of the Si/SiC rod and a coating made from Ferro frit #3249 are very close, i.e. about $4.5 \times 10^{-6}$°C.$^{-1}$. Thermal expansion coefficients between $0.1 \times 10^{-6}$°C.$^{-1}$ and $9 \times 10^{-6}$°C.$^{-1}$ are acceptable so long as the coefficients of the rod and the coating are about the same. The softening point of the coating is about 1000°C., which is much higher than the melting temperature of the molten metal. A softening point slightly above the melting point of the particular molten metal is acceptable, e.g. 750°C. for Al.

Probe 14 is attached to one side of container 10 by insulated clamp 22. Probe 14 is physically removed from probe 16. Probe 16 is preferably made of graphite or stainless steel, and thus, is highly electrically conductive. Probe 16 is connected to the other side of container 10 by insulated clamp 24.

The conductive inner rod 18 of probe 14 is connected by wire 26 to AC voltage source 28. Preferably, the voltage source is AC. Alternatively, however, a simple DC battery will suffice.

Conductive probe 16 is connected by wire 32 to current detector 30 which is preferably a digital multimeter, which includes an ammeter. Multimeter 30 and voltage source 28 are electrically connected together through resistor 32, which regulates the current in the circuit. Preferably, resistor 32 is a 100 Ohm resistor, and preferably, the voltage source 28 generates 6 volts. While the use of an ammeter to measure current is preferred, similar results may be obtained by measuring the resistance of the circuit.

Typically, when Cl$_2$ gas is injected into the molten Al alloy 12 using a rotating disc diffuser, extremely small droplets of molten AlCl$_2$ and MgCl$_2$ are formed. If substantially no molten chlorides are present in molten metal 12, the circuit 25 will remain open, i.e. there will be no current flowing in the circuit or between the probes since coating 20 is nonconductive and is nonwettable by the molten metal. However, if there is an amount of molten salt in molten metal 12, the salt will wet the coating 20, thereby forming an electrically conductive path through the coating at the place where the wetting occurs. The wetting occurs when enough salt is collected on the surface of the coating 20. The molten salt, which wets the coating, will be absorbed into the open pores of the coating by capillary action and establish a conductive bridge between the conductive rod 18 and the molten metal. This wetting will result in an electrical current flowing in circuit 25, including a current flowing between probes 14 and 16 through the wetted coating 20 and through the molten metal 12. The current will be detected by multimeter 30.

The Ferro frit referred to above to coat a SiC rod 18 was prepared as set forth below:

The as-received Ferro frit was attrition milled using water only and a Union Process attritor. A slurry containing 60% by weight of slurry was obtained, with very fine particle size. 160 g of this slurry was mixed with 100 g of the as-received, coarser, Ferro frit powder, so that a 50/50 ratio was obtained, on a dry powder basis. 234 g of deionized water was added to bring the solids content to 40% by weight. Then 88 g of an aqueous gel containing 2.5% of Kelzan M (a thickening agent) and of Darvan C (a dispersant) were added. The solids content of the final slurry was 34% by weight.

The objective was to obtain a broad particle size distribution for high packing density and low firing shrinkage, to prevent cracks on firing. Also, a high viscosity of the slurry prevented running after the rod was withdrawn from the slurry and allowed uniform surface coating. Finally, a relatively low solids loading was needed to limit the coating thickness and avoid firing cracks.

The prepared frit was applied to the cylindrical rod 18 as set forth below:

The as-received rods were rounded at one end by machining with a diamond coated wheel and thoroughly degreased with hot NaOH, rinsed with deionized water and dried. Afterwards, they were handled only with latex gloves.

About 100 ml of slurry was placed in a Pyrex cylinder and vigorously shaken. The SiC rod was immersed in the slurry, kept for about 30 seconds, withdrawn and shaken gently several times, to remove excess slurry from surface. Shaking was ended when no drops were falling from the rounded end. The coated rod was then kept vertical to dry with the rounded end up. The dry coated rod was then fired in an electric furnace. The furnace temperature was raised to 750° C. in six hours, held at 750° C. for one hour, and then brought back to room temperature in three hours.

The first coating did not completely cover the rough surface and therefore the coating/drying/firing procedure was repeated. The rod with two coatings was inspected under an optical microscope and showed no cracks. Only a few small pinholes were visible, probably caused by air bubbles in the slurry.

Two rods were coated three times to check whether cracking would occur on a thicker coating. No cracking was observed and the number of pinholes was reduced.

FIG. 3 is a photomicrograph of a cross section of the coated rod of FIG. 1 including solidified Al alloy metal. FIG. 3 was made utilizing secondary electrons with an image magnification of 100×. FIG. 3 illustrates the porous micro topography of nonconductive layer 20. Wetting of this microporous nonconductive layer 20 by a liquid salt will cause a bridging of the microporous layer between the SiC rod 18 and the metal 21.

The following experiments were conducted in order to show that the apparatus set forth herein is useful in detecting the presence of molten salts in molten Al alloy.

Experiment #1:

Two stainless steel (S.S.) rods, 1 cm diameter and 30 cm long, were connected to a 6 V battery and a 100 Ohm resistor and the free ends of the rod shorted with a copper wire. A current of 57 mA was measures. No molten Al alloy was used. From Ohm's law, the current should be 60 mA if other resistances are zero.

Experiment #2:

Two rods, one SiC, uncoated, and the other of S.S., were connected as in Experiment #1 above. The measured current was also 57 mA. (The resistance of the SiC and S.S. rods is about the same.)

Experiment #3:

A coated SiC rod which was prepared in accordance with the teachings as set forth above, with two coatings/two firings was immersed into salt-free molten Al alloy, after skimming the dross above it, and connected to the positive pole of the 6 v battery. A S.S. rod was connected to the negative pole. Both rods were immersed in the molten Al alloy to a depth of about 6 cm. A current of 2.4 mA was measured, which dropped to 0.43 mA after about 3 mins. This experiment shows that the frit coating is impervious to the molten metal.

Experiment #4:

A SiC rod, uncoated, and a S.S. rod, connected to the battery as in Experiment #3, were both immersed in the molten Al alloy, to a depth of about 8 cm. A current of 57 mA was measured, which was constant for about 5 mins. This experiment demonstrates the conductivity of the two rods and of the molten Al.

Experiment #5:

A SiC rod with two coatings/two firings was preheated with a propane torch and a few crystals of $MgCl_2 \cdot 6H_2O$ were deposited on the coating about 5 cm from the rounded end. The crystals melted and were absorbed by the coating. This rod and a S.S. rod, connected to the battery as in Experiment #3, were immersed in the molten Al alloy to a depth of about 15 cm. A current of 37 mA was immediately measured, which kept increasing up to 55 mA after about 15 mins. This experiment demonstrates that molten $MgCl_2$ formed a conducting bridge between the SiC and the molten alloy.

Experiment #6:

A SiC rod with two coatings/two firings, connected to the battery as in Experiment #3, was immersed, together with a S.S. rod, into the salt-free molten Al alloy. The SiC rod was slowly rotated at 3 RPM describing a circle of about 7 cm diameter in the molten metal. The current was measured after several intervals, during a period of 15 hrs. The current never exceeded 0.9 mA, and most of the time was about 0.2 mA. This experiment demonstrates the stability of the coating under conditions simulating the flow of molten metal encountered in commercial Al cast shops.

Experiment #7:

A SiC rod similar to that used in Experiment #6 above was immersed in the molten metal and turned constantly at 3 RPM for about 4 hrs. An S.S. rod was also immersed. Both rods were attached to the battery as in Experiment #3. The measured current was always about 0.2 mA. After 4 hrs, an uncoated SiC rod containing some $AlCl_3$ and $Al(NO_3)_3$ was immersed into the molten metal and removed. Reddish-brown fumes evolved and after about 20 mins a current of 37 mA was measured. The coated SiC rod was kept turning for 15 more hrs and the current measured at the end of this period was 25 mA. This experiment demonstrates that molten salt contaminated the alloy and was detected by the probe.

It is preferred that the bottom portion 15 of the SiC probe be rounded so that there are no sharp edges on the coated portion of the probe which might lead to an imperfection in the coating, thereby enabling the molten metal to contact the conductive portion 18 of the probe.

The invention may be embodied in other forms or carried out in other ways without departing from the true spirit and essential characteristics thereof. For example, other materials and geometries may be used. The present embodiment is therefore to be considered in all respects illustrative and not restrictive, the scope of the invention being indicated by the appended claims, and all changes and other embodiments which come within the meaning and range of equivalencies are intended to be embraced therein.

We claim:

1. A device for use in detecting the presence of molten salt in molten metal comprising:

a substrate adapted to at least be partially submerged in molten metal; said substrate including an electrically conductive surface; said conductive surface of said substrate being coated with an electrically nonconductive porous material; said nonconductive material being wettable by the molten salt but nonwettable by the molten metal, whereby a conductive path through said nonconductive material is created by the presence of the salt in the molten metal.

2. A device as set forth in claim 1, wherein said molten metal is taken from the group consisting of Al or Al alloy.

3. A device as set forth in claim 1, wherein said substrate is a probe.

4. A device as set forth in claim 1, wherein the thickness of said coating of said nonconductive material is less than 8 millimeters.

5. A device as set forth in claim 4, where said thickness of said coating is between 0.001 millimeter and 8 millimeters.

6. A device as set forth in claim 1, wherein said nonconductive material and said conductive substrate surface have substantially similar thermal expansion coefficients.

7. A device as set forth in claim 6, wherein said thermal expansion coefficients are between $0.1 \times 10^{-6} °C.^{-1}$ and $9 \times 10^{-6} °C.^{-1}$.

8. A device as set forth in claim 7, wherein said thermal expansion coefficients are about $4.5 \times 10^{-6} °C.^{-1}$.

9. A device as set forth in claim 1, wherein said coating is substantially inert to the molten metal.

10. A device as set forth in claim 1, wherein said coating is substantially free of cracks and pinholes.

11. A device as set forth in claim 1, wherein the softening point of said nonconductive material is substantially higher than the melting point of the molten metal.

12. A device as set forth in claim 11, wherein said softening point of said nonconductive material is greater than 750° C.

13. A device as set forth in claim 1, wherein said nonconductive material is a ceramic which is not wetted by molten metal.

14. A device as set forth in claim 13, wherein said ceramic is taken from the group consisting of oxides and non-oxides.

15. A device as set forth in claim 14, wherein the range of the composition by weight of said nonconductive material is 0% to 5% CaO, 0% to 22% MgO, 2% to 50% $Al_2O_3$, 0% to 50% $B_2O_3$ and 15% to 80% $SiO_2$.

16. A device as set forth in claim 15, wherein the composition by weight of said nonconductive material is 3.5% CaO, 12.2% MgO, 13.3% $Al_2O_3$, 28.9% $B_2O_3$ and 42.1% $SiO_2$.

17. A device as set forth in claim 1, wherein the conductive surface of said substrate is an electrically conductive metal, a conductive ceramic, or a metal/ceramic composite.

18. A device as set forth in claim 16, wherein said conductive surface is taken from the group consisting of SiC, the combination of Si and SiC, and the combination of C and SiC.

19. A device as set forth in claim 1, wherein said conductive surface of said substrate is rough for enhancing adhesion.

20. A device as set forth in claim 2, wherein said probe is in the form of a rod.

21. A device as set forth in claim 20, wherein said rod has a rounded bottom.

22. An apparatus for use in detecting the presence of molten salt in molten metal comprising:

a container receiving an amount of molten metal;

a first substrate and a second substrate; said first substrate not in direct physical contact with said second substrate; each of said first and second substrates being partially submerged in the molten metal; said first substrate including an electrically conductive surface; said conductive surface of said first substrate being coated with an electrically nonconductive material; said nonconductive material being wettable by molten salt but nonwettable by the molten metal, whereby a conductive path through said nonconductive material is created by the presence of molten salt in the molten metal;

said second substrate having a conductive surface;

an electrical circuit connected to said first and second substrates; said circuit including a voltage source and a current detector, whereby said current detector will detect a higher current in said circuit when molten salt is present in the molten metal than when molten salt is not present in the molten metal.

23. An apparatus as set forth in claim 22, wherein said molten metal is taken from the group consisting of Al and Al alloy.

24. An apparatus as set forth in claim 22, wherein said substrate is a probe.

25. An apparatus as set forth in claim 22, wherein the thickness of said coating of said nonconductive material is less than 8 millimeters.

26. An apparatus as set forth in claim 25, where said thickness of said coating is between 0.001 millimeter and 8 millimeters.

27. An apparatus as set forth in claim 22, wherein said nonconductive material and said conductive substrate surface have substantially similar thermal expansion coefficients.

28. An apparatus as set forth in claim 27, wherein said thermal expansion coefficients are between $0.1 \times 10^{-6} °C.^{-1}$ and $9 \times 10^{-6} °C.^{-1}$.

29. An apparatus as set forth in claim 28, wherein said thermal expansion coefficients are about $4.5 \times 10^{-6} °C.^{-1}$.

30. An apparatus as set forth in claim 22, wherein said coating is substantially inert to the molten metal.

31. An apparatus as set forth in claim 22, wherein said coating is substantially free of cracks and pinholes.

32. An apparatus as set forth in claim 22, wherein the softening point of said nonconductive material is substantially higher than the melting point of the molten metal.

33. An apparatus as set forth in claim 32, wherein said softening point of said nonconductive material is greater than 750° C.

34. An apparatus as set forth in claim 22, wherein said nonconductive material is a ceramic which is not wetted by molten metal.

35. An apparatus as set forth in claim 22, wherein said nonconductive material is a composition of CaO, MgO, $Al_2O_3$, $B_2O_3$ and $SiO_2$.

36. An apparatus as set forth in claim 22, wherein the range of said composition by weight of nonconductive material is 0% to 5% CaO, 0% to 22% MgO, 2% to 50% $Al_2O_3$, 0% to 50% $B_2O_3$ and 15% to 80% $SiO_2$.

37. An apparatus as set forth in claim 36, wherein said composition by weight of nonconductive material is 3.5% CaO, 12.2% MgO, 13.3% $Al_2O_3$, 28.9% $B_2O_3$ and 42.1% $SiO_2$.

38. An apparatus as set forth in claim 22, wherein the conductive surface of said substrate is an electrically conductive metal, a conductive ceramic, or a metal/ceramic composite.

39. An apparatus as set forth in claim 37, wherein said conductive surface is taken from the group consisting of SiC, the combination of Si and SiC, and the combination of C and SiC.

40. An apparatus as set forth in claim 22, wherein said conductive surface is rough for enhancing adhesion.

41. An apparatus as set forth in claim 23, wherein said probe is in the form of a rod.

42. An apparatus as set forth in claim 41, wherein said rod has a rounded bottom.

43. A method for detecting the presence of salt in molten metal utilizing a container receiving an amount of molten metal including a first substrate and a second substrate, each of which are at least partially submerged in said molten metal; said first substrate including an electrically conductive surface; said conductive surface of said first substrate being coated with an electrically nonconductive material; said nonconductive material being wettable by the salt but nonwettable by the molten metal; said first and second substrates connected to an electrical circuit; said method comprising the steps of:

applying a voltage to said circuit; and measuring the current or resistance in said circuit.

* * * * *